United States Patent
Vermeulen et al.

(10) Patent No.: US 9,775,528 B2
(45) Date of Patent: Oct. 3, 2017

(54) PHOTOPLETHYSMOGRAPHY SENSOR APPARATUS AND METHOD

(71) Applicant: KONINKLIJKE PHILIPS N.V., Eindhoven (NL)

(72) Inventors: Olaf Thomas Johan Antonie Vermeulen, Eindhoven (NL); Koen Geenen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/912,418

(22) PCT Filed: Jun. 19, 2015

(86) PCT No.: PCT/EP2015/063858
§ 371 (c)(1),
(2) Date: Feb. 17, 2016

(87) PCT Pub. No.: WO2016/000986
PCT Pub. Date: Jan. 7, 2016

(65) Prior Publication Data
US 2017/0042435 A1     Feb. 16, 2017

(30) Foreign Application Priority Data

Jun. 30, 2014 (EP) .................................. 14174974.7

(51) Int. Cl.
*A61B 5/08*         (2006.01)
*A61B 5/024*      (2006.01)
*A61B 5/00*        (2006.01)

(52) U.S. Cl.
CPC ...... *A61B 5/02416* (2013.01); *A61B 5/02427* (2013.01); *A61B 5/7203* (2013.01)

(58) Field of Classification Search
CPC ....................................................... A61B 5/08
(Continued)

(56) References Cited

U.S. PATENT DOCUMENTS 4,258,719 A    3/1981   Lewyn
4,353,152 A    10/1982   O'Connor
(Continued)

FOREIGN PATENT DOCUMENTS

JP     H01259840 A    10/1989
JP     2000139862 A    5/2000
(Continued)

OTHER PUBLICATIONS

"Understanding Flash ADCs", Maxim Integrated Products, Inc., Sep. 2010.

*Primary Examiner* — Carl H Layno
*Assistant Examiner* — Jon Eric C Morales

(57) ABSTRACT

The present invention relates to a photoplethysmography sensor apparatus (200, 300), a photoplethysmography sensor method (400), and a photoplethysmography sensor computer program product. It is proposed to measure a photoplethysmographic signal without ambient light interference. Ambient light signals are rejected by subtraction of a compensation current at the input of a transimpedance amplifier (240, 340). The compensation current is controlled via a closed loop, without interfering with the low duty cycle operation of a photoplethysmography LED (210, 310).

14 Claims, 2 Drawing Sheets

(58) Field of Classification Search
USPC .................................................. 600/529, 534
See application file for complete search history.

(56) References Cited

U.S. PATENT DOCUMENTS

| | | | |
|---|---|---|---|
| 5,177,565 | A | 1/1993 | Stoughton |
| 5,853,372 | A | 12/1998 | Britton |
| 5,954,644 | A | 9/1999 | Dettling |
| 6,381,479 | B1 | 4/2002 | Norris |
| 7,740,591 | B1 | 6/2010 | Starr |
| 2009/0005662 | A1 | 1/2009 | Petersen |
| 2010/0324384 | A1 | 12/2010 | Moon |

FOREIGN PATENT DOCUMENTS

| | | | | |
|---|---|---|---|---|
| JP | 2010004972 A | | 1/2010 | |
| JP | 2013514823 A | | 5/2013 | |
| NL | WO 2016000986 A1 | * | 1/2016 | .......... A61B 5/7203 |
| WO | 2005009221 A2 | | 2/2005 | |
| WO | 2006083180 A1 | | 8/2006 | |
| WO | 2011077294 A1 | | 6/2011 | |
| WO | 2013077808 A1 | | 5/2013 | |

* cited by examiner

PHOTOPLETHYSMOGRAPHY SENSOR APPARATUS AND METHOD

CROSS-REFERENCE TO PRIOR APPLICATIONS

This application is the U.S. National Phase application under 35 U.S.C. §371 of International Application No. PCT/EP2015/063858, filed on Jun. 19, 2015, which claims the benefit of European Patent Application No. 14174974.7, filed on Jun. 30, 2014. These applications are hereby incorporated by reference herein.

FIELD OF THE INVENTION

The invention relates to a photoplethysmography sensor apparatus, a photoplethysmography sensor method, and a photoplethysmography sensor computer program.

BACKGROUND OF THE INVENTION

Photoplethysmography (PPG) refers to acquiring a volumetric organ measurement by optical means. Frequently, pulse oximeters are employed, which detect changes in light absorption properties of the human skin. Typically, a transmissive or reflective blood PPG sensor monitors the perfusion of blood to the dermis and subcutaneous tissue of the skin through absorption measurement at a specific wavelength. Besides light originating from blood, there is a far greater portion of light detected, which originates from tissue and ambient light.

Photoplethysmography signals comprise a very small AC signal (the actual plethysmogram) on top of a very large (unwanted) DC offset signal. The DC offset signal comprises signals originating from skin and tissue, and from a considerable part of ambient light. Unfortunately, the amount of ambient light detected is not constant, but varies due to changing ambient light conditions and due to motion artifacts (caused, e.g., by the coupling between the photoplethysmography sensor and the skin). The temporal rate of change of detected ambient light includes frequencies in the photoplethysmography frequency band of interest. This prohibits simple frequency domain filtering, because filtering out these frequencies (in the hope of suppressing the detected ambient light) would also filter (or significantly suppress) frequencies of the photoplethysmography frequency band of interest.

Currently known mechanisms for ambient light rejection include for example DC-restore circuits, which sample the ambient light periodically when the photoplethysmography excitation light (such as, e.g., a light-emitting diode, LED) is temporarily turned off. In a different time slot (e.g., when the LED is turned on) a sample is taken which contains both ambient and the photoplethysmography signal. By subtracting the signal with the photoplethysmography excitation light turned off from the signal with the photoplethysmography excitation light turned on, an "offset-corrected" photoplethysmography signal is obtained, which does not exhibit interference from ambient light. Typically, this sampling is done after a transimpedance amplifier (TIA) has converted and amplified the photocurrent generated by the detector into a voltage. Alternatively and/or additionally, this sampling is done completely in the digital domain after the signal has been processed by an analog-to-digital converter (ADC).

A number of problems and disadvantages are present in conventional photoplethysmography sensors. First, the amount of ambient light detected can be considerable. This means that when designing the amplifier, a certain amount of the dynamic range available must be reserved for properly detecting the ambient light, resulting in a sub-optimal amplifier design.

Additionally, if the subtraction of the ambient signal is done in the digital domain (i.e., after analog-to-digital conversion), then a number of ADC bits have to be reserved for the ambient light. Reserving ADC bits for the ambient light however limits the resolution available for photoplethysmography signals.

However, if the subtraction is done directly after processing by the TIA, a sample-and-hold circuit is needed to hold the ambient value (i.e., the measurement value corresponding to the ambient light) until the next sampling period of the photoplethysmography signal. The gain accuracy of this sample-and-hold signal determines the efficacy of the compensation.

One option to address the problems of conventional photoplethysmography sensors is to employ a factory calibration step of the sample-and-hold element. Such an additional factory calibration step however adds manufacturing costs and is thus less preferable.

U.S. Pat. No. 7,740,591 discloses a plethysmography sensor. This sensor comprises an ambient light canceling circuit that receives the output of transimpedance differential amplifiers. The ambient light canceling circuit operates as follows: when timing control circuit has both the Red and IR LED's off, the ambient light is the only light the sensor has for an output. The Ambient light is sampled, and the value of the signal is held in a capacitor tied to ground using a FET. When the FET is turned off, the value stored in the capacitor is used in the path of the Red and IR signal string. This stored value in the capacitor removes the error of the ambient light.

U.S. Pat. No. 6,381,479B1 discloses a system for providing an improved DC and low frequency signal rejection in a photoplethysmographic measurement instrument. The system is used in a measurement instrument which includes at least two signal sources for transmitting light signals at least at two wavelengths through a tissue of a test subject and a detector for converting light signals transmitted through the tissue into a detector output signal. The system includes a DC restoration which removes DC and low frequency signal components from the detector output signal prior to amplification thereof so as to avoid saturating amplified output signal with the low frequency signal component. The DC restoration is configured to continuously remove low frequency signal component from the detector signal during dark intervals when the signal sources are deactivated, as well as during light intervals when one of the signal sources is activated. In one embodiment, the DC restoration is embodied in the form of a DC restoration circuit which comprises a transimpedance amplifier which receives the detector output signal and produces an amplifier output signal and an integrator feedback loop which receives the amplified output signal and produces a bias current, wherein the bias current is used to subtract DC and low frequency signal components from the detector output signal prior to amplification of the detector signal by the amplifier.

SUMMARY OF THE INVENTION

It is an object of the present invention to provide an improved photoplethysmography sensor apparatus, an improved photoplethysmography sensor method, and an improved photoplethysmography sensor computer program that overcome the problems associated with prior-art PPG sensors.

In a first aspect of the invention, there is provided a photoplethysmography sensor apparatus comprising a light source unit configured to generate a first light signal; and a photodetector unit configured to observe a second light signal, where said second light signal is indicative of an absorption of said first light signal in a target wherein said photodetector unit is further configured to output a photodetector output signal in response to observing said second light signal. The apparatus further comprises an ambient light compensating feedback loop comprising a track-and-hold unit configured to receive a photodetector output signal. The apparatus is configured to compare an output signal of said track-and-hold unit to a reference signal and the ambient light compensating feedback loop comprises a first amplifying unit configured to provide a compensation current based on said comparison to the track-and-hold unit.

The present invention proposes to measure a photoplethysmographic signal without ambient light interference. Ambient light signals are rejected by providing a compensation current at the input of the track-and-hold unit directly or via, for example, a transimpedance amplifier. The compensation current is preferably controlled via a closed loop, without interfering with the low duty cycle operation of the light source unit (such as, e.g., a photoplethysmography excitation LED). In other words, the present invention proposes to overcome the above-noted problems by subtracting a compensation current directly at the input of the amplifier. This current is controlled via a feedback loop which ensures that no ambient light current will enter the TIA. This eliminates the aforementioned problems. Said track-and-hold unit preferably comprises a track-and-hold circuit. By employing a track-and-hold unit, i.e., preferably a track-and-hold circuit, the present invention is well-suited for "AC kind" of ambient light, such as, e.g., artificial light and sunlight, as occurring, e.g., during running. The term "AC kind of ambient light" as used herein means that, e.g., during running, ambient light intensity varies (e.g., because the runner is swinging his/her arm periodically while running) thereby resulting in an alternating current being observed by the photodetector. The alternating current may be periodic, but that is not necessarily the case. Also step-like changes which may be caused, e.g., by a jump of the user are covered. A track-and-hold-circuit is thus preferable to, e.g., an integrate-and-hold circuit, where the light-emitting diode is pulsed with an as low as possible duty cycle. Accordingly, the ambient light is integrated during a chosen period so as to use that history for compensation during a short measurement period. It is noted that integrate-and-hold circuits do not necessarily integrate over long periods. The integration time can be chosen as short desired. However, the integration part implies a low-pass filter action, and therefore is less suited for 'AC kind' of ambient light. The use of an integrating action in the negative feedback loop implies ensuring zero DC error because any non-zero DC signal will increase the error signal by integration. This cannot be achieved with a track-and-hold topology, because there the error can only become zero at infinite amplification. In the present case, it is however not necessary to have a zero DC error. Rather, ambient light is to be attenuated as much as possible to free up dynamic range. Furthermore, by providing an ambient light correcting feedback loop that is (preferably always, i.e., permanently) closed, the tracked part of the signal is always insignificantly small within the loop. As PPG signals are small (especially in reflective mode PPG sensors), ambient light levels can be relatively high. If the ambient part of the current was not continuously subtracted, an amplifier (such as, e.g., a transimpedance amplifier) receiving light from said photodetector unit would have to settle to large ambient light steps during each correction cycle. In the present configuration, this is not the case. The present embodiment thereby allows for relaxing the dynamic requirements on the PPG sensor apparatus. PPG sensors typically employ at least one amplifier. However, a PPG sensor may also use a phototransistor instead of a photodiode. A phototransistor has gain and is therefore an amplifier although it is not always explicitly visible as an amplifier if one views it as the detector. The same is true for any other photo detector with internal gain.

In a further preferred embodiment, said first amplifying unit comprises a trans-conductance amplifier. Since said first amplifying unit comprises a trans-conductance amplifier, the difference between the track-and-hold unit's output signal and the reference signal is preferably converted to a compensation current by means of said trans-conductance amplifier. As a consequence, it is possible to subtract the compensation current already at the input of the second amplifier. In a further preferred embodiment, wherein said trans-conductance amplifier comprises a resistor and/or a voltage controlled current source. By definition trans-conductance is the reciprocal of resistance and thus has the dimension current divided by voltage, or in other words a current dependent on a voltage (i.e., a voltage controlled current source).

In a further preferred embodiment, said photoplethysmography sensor apparatus comprises an analog-to-digital converter configured to receive the output signal from said second amplifying unit. In practice, modern PPG and $SpO_2$ sensors have an analog front end followed by a digital processing part and thus require an ADC.

In a further preferred embodiment, said photoplethysmography sensor apparatus further comprises a light source driver unit configured to control said light source unit. Preferably, the light source unit comprises a pulsed LED. Employing pulsed LEDs is preferable for wearable devices for battery saving reasons and ambient sampling. Employing pulsed LEDs is further preferable for medical devices with regard to ambient sampling and also because of color sequential reasons in $SpO_2$ sensors.

In a further preferred embodiment, said photoplethysmography sensor apparatus further comprises a synchronous detector. By employing a synchronous detector, ambient light that is not synchronous with the light signal output from said light source unit is preferably cancelled or at least suppressed.

In a further preferred embodiment, said photoplethysmography sensor apparatus further comprises a light source driver unit configured to control said light source unit and wherein said synchronous detector is configured to operate synchronously with said light source driver unit. By having said synchronous detector and said light source driver unit operate synchronously, said photoplethysmography sensor apparatus is preferably configured such that only ambient light that is synchronous with light from said light source unit contributes a background signal to light reflected from said target. In contrast, light that is not synchronous with the light signal output from said light source unit is preferably cancelled or at least suppressed.

In a further preferred embodiment, said photoplethysmography sensor apparatus comprises an analog-to-digital converter configured to receive the output signal from said synchronous detector. Employing an analog-to-digital converter in combination with said synchronous detector is preferable for the following reasons. A synchronous detector may be implemented in the analog or in the digital domain. Using it in the analog domain has the advantage that after the synchronous detection (which preferably includes the low pass filter) the bandwidth is limited to what is needed (for instance, approximately 15 Hz) and that all asynchronous interference has been removed. This means that a low speed high resolution ADC can be used. If SD is done in the digital domain then the bandwidth requirements are higher (depending on the LED pulse frequency) and thus AD conversion will be more expensive and/or less accurate. Furthermore, asynchronous interference is still present and needs to be considered in ADC selection. The advantage of implementing a synchronous detector in the digital domain involves an increased flexibility (because it is software and/or programmable) and, because less external components are needed. Further advantages of implementing a synchronous detector in the digital domain relate to smaller size and potentially lower power consumption.

In a further preferred embodiment, said synchronous detector comprises a synchronous rectifier followed by a low pass filter. In a further preferred embodiment, said synchronous rectifier multiplies the signal with +1 or −1.

In a further preferred embodiment, said photoplethysmography sensor apparatus further comprises a microcontroller configured to adjust said reference signal.

Typical use-cases for adjusting the reference signal include offset compensation or level shifting, e.g. into the ADC range. The corrected output signal will "ride on/off" said reference signal. This means that with the LED off, the output of the second amplifying unit will be the reference signal. With the LED on, it will be higher or lower depending on the direction (i.e., the connection) of the photodiode. Deviation from 0V would preferably by chosen for single supply circuits (such as, e.g., battery operated devices) to level shift the signal above reference (0 V).

In a further preferred embodiment, said photoplethysmography sensor apparatus comprises a subtractor unit. By employing a subtractor unit, the difference between said reference signal and said output signal from said track-and-hold unit can be determined.

In a further preferred embodiment, said photodetector unit comprises a photo diode and/or transistor.

In a further preferred embodiment, the photoplethysmography sensor apparatus further comprises a second amplifying unit for amplifying a sum of the compensation current and the photodetector output signal and for delivering an amplified signal to an input of the track and hold unit. The second amplifying unit may comprise a transimpedance amplifier. Standard layouts of transimpedance amplifiers can be found, e.g., in the book *"Photodiode Amplifiers: Op Amp Solutions"*, Mcgraw Hill Book Co (1995) by J. Graeme.

In a further preferred embodiment, said photoplethysmography sensor apparatus further comprises a sample-and-hold circuit configured to store a signal output by said transimpedance amplifier. Preferably, the light source unit (such as, e.g., an LED) is driven with a low duty cycle to save battery power. This means that there is only a short period available for sampling the actual photoplethysmography signal. A sample-and-hold circuit will extend this time. However, many modern ADCs (typically referred to as sampling ADCs) already include a sample-and-hold component. Therefore, including a sample and hold circuit will provide an advantage, e.g., in case it is desired to avoid using an ADC in order to save costs and/or space by using the hardware already present in a microcontroller. There are several known possibilities to build a (low speed) ADC using a microcontroller. One possibility refers to building an SAR-ADC by using a microcontroller's analog output in combination with its voltage comparator.

In a further preferred embodiment, said light source comprises a light emitting diode. Other types of light sources may include semiconductor lasers/VCSELs.

In a further preferred embodiment, said synchronous detector comprises a digital lock-in amplifier. Preferably, a synchronous detector may be implemented as a synchronous rectifier (e.g., multiplying synchronously by ±1) followed by a low-pass filter. Further preferably, a lock-in amplifier may correspond to a device that multiplies the input signal with a synchronous cosine and sine reference (i.e., an in-phase (I) and an quadrature (Q) component), followed by a low pass filter and a computation of the amplitude $\sqrt{I^2+Q^2}$. Because it involves a computation, the lock-in is preferably implemented in the digital domain. In a further preferred embodiment, said synchronous detector is arranged within said microcontroller. Arranging the synchronous detector within the microcontroller is preferred due to space reasons, lower costs and less supply current. The preferred embodiment is preferably used in an analog synchronous detector implementation: In a synchronous detector that does not use quadrature demodulation (i.e., where only one synchronous rectification is preformed), the phase shift between the measured signal and the reference is preferably translated into a DC offset in the output. Since this phase shift will be almost completely fixed (e.g., the impact of the optical path length variation is not significant, because of the speed of light), it can be compensated by adjusting the reference signal (i.e., preferably a reference voltage).

According to a second aspect of the present inventions, there is provided a photoplethysmography sensor method comprising the steps of
  generating a first light signal by a light source unit;
  observing a second light signal by a photodetector unit, wherein said second light signal is indicative of an absorption of said first light signal in a target;
  receiving, in response to observing said second light signal, a photodetector output signal by an ambient light compensating feedback loop comprising a track-and-hold unit and an amplifying unit;
  comparing an output signal of the track-and-hold unit to a reference signal, wherein said output signal of said track-and-hold unit is based on said photodetector output signal; and
  providing a compensation current by the amplifying unit to the track-and-hold unit based on said comparison.

According to a third aspect of the present invention, there is provided a photoplethysmography sensor computer program product comprising a computer readable memory storing computer program code means for causing the photoplethysmography sensor apparatus to carry out the steps of the photoplethysmography sensor method, when the computer program is run on a computer controlling the photoplethysmography sensor apparatus.

It shall be understood that the photoplethysmography sensor apparatus of claim 1, the photoplethysmography sensor method of claim 13 and the photoplethysmography sensor computer program of claim 14 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

The present invention relates to a photoplethysmography sensor apparatus, a photoplethysmography sensor method, and a photoplethysmography sensor computer program. It is proposed to measure a photoplethysmographic signal without ambient light interference. Ambient light signals are rejected by subtraction of a compensation current at the input of a transimpedance amplifier. The compensation current is controlled via a closed loop, without interfering with the low duty cycle operation of a photoplethysmography LED.

Figure 1:
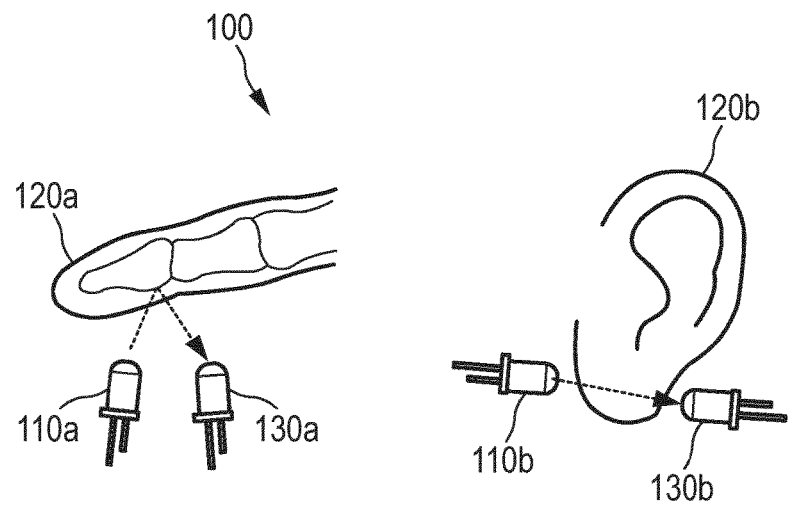
FIG. 1 illustrates the basic principle of photoplethysmography.

FIG. 1 illustrates the basic principle of PPG. PPG refers to acquiring a volumetric organ measurement by optical means. In example 100 shown in FIG. 1, a light-emitting diode 110a outputs light towards a human finger 120a. The light is partly absorbed and partly reflected by finger 120a. Reflected light is observed by photo diode or transistor 130a. Further, in example 100, a light-emitting diode 110b outputs light towards a human earlobe 120b. The light is partly absorbed and partly transmitted by earlobe 120b. Transmitted light is observed by photo diode or transistor 130b. The light observed by photo diode or transistor 130a, 130b is indicative of the amount of light absorbed within target 120a, 120b. The observed light can thus be used to derive information on the target structure.

Figure 2:
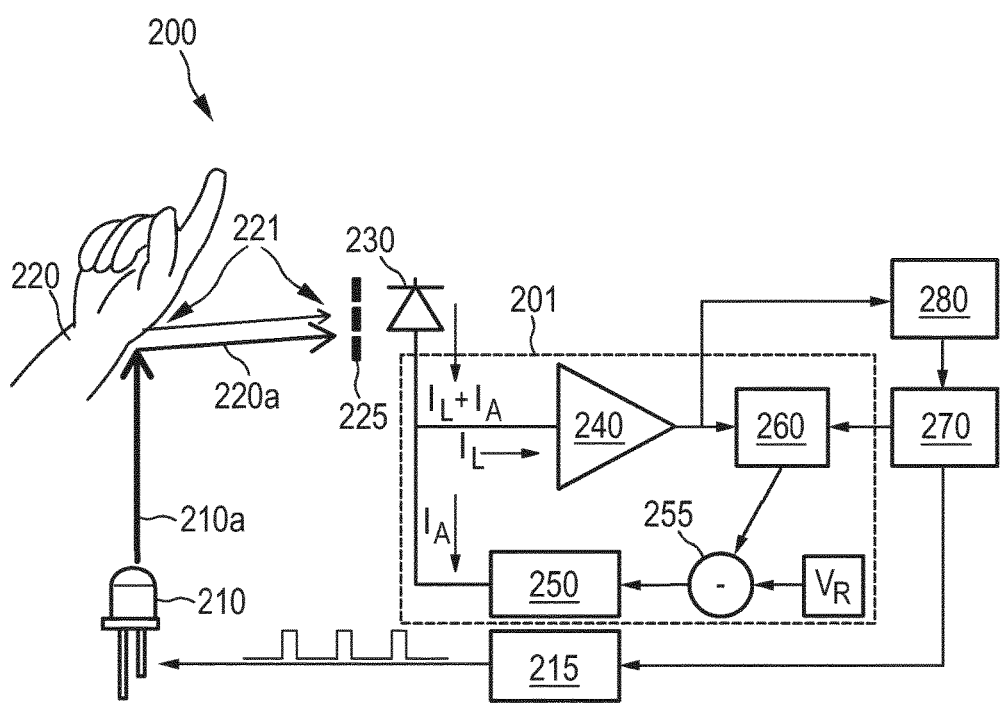
FIG. 2 shows schematically and exemplarily an embodiment of a photoplethysmography sensor apparatus.

FIG. 2 shows schematically and exemplarily an embodiment of a photoplethysmography sensor apparatus 200. LED 210 is periodically turned on and off by LED driver 215. This saves power, but also allows sampling ambient light when the LED 210 is turned off. Light 210a emitted by LED 210 is directed towards tissue, such as, in the example shown, human wrist 220. Reflected light 220a is observed by a photo diode 230. Reflected light 220a may additionally be filtered by an optional optical filter 225. Further to reflected light 220a, photo diode 230 will observe interference from ambient light 221. For the case that LED 210 is switched on, photo diode 230 will thus generate a combined current comprising an LED component $I_L$ and an ambient light component $I_A$.

Current PPG sensors typically use a sample-and-hold circuit to 'store' an ambient sample. Thus, once a PPG signal becomes available, a correction step can be applied thereto based on the stored ambient sample. In a preferred embodiment of photoplethysmography sensor apparatus 200, it is proposed to directly subtract a compensating current $I_A$ from the input rather than to store an ambient sample, from which a background level is derived to correct the observed signal afterwards. A closed ambient light compensating feedback loop 201 ensures that the output of TIA 240 corresponds to a reference voltage $V_R$. By maintaining this procedure, a PPG signal will thus also be compensated when LED 210 is on. Accordingly, it is proposed to employ a track-and-hold circuit 260 to steady ambient light compensating feedback loop 201 when a PPG signal is taken.

Photoplethysmography sensor apparatus 200 may be described as follows:

During a first time period, light-emitting diode 210 is turned off. Track-and-hold circuit 260 is in "track-mode". A track-and-hold (or sample-and-hold, SHA) element stores an analog value for a certain amount of time. It thus converts a continuous time signal into a discrete time signal. An integrate-and-hold does not store the input itself, but it stores an integral of the input. (Integrate-and-hold elements are also referred to as integrating-sample-and-hold elements.) In the track-and-hold element, the output follows the input while in track mode. When switched to hold-mode, the last input level is hold. The integrate-and-hold element integrates the input signal during the integrate-mode and stores the integrated value (not equal to the input) when it is switched to hold-mode. The output of track-and-hold circuit 260 is compared to reference voltage $V_R$ (which may be, e.g., a zero voltage or some other desired DC voltage level). The difference obtained from said comparison (e.g., obtained by means of subtractor circuit 255) is subsequently converted to a compensation current by means of a first amplifying unit 250, which may be, e.g., a trans-conductance amplifier 250. Trans-conductance amplifier 250 may be, e.g., a resistor or voltage controlled current source, but any other trans-conductance amplifying means are suitable as well. Reference voltage $V_R$ may be fixed or controlled e.g. by microcontroller 270.

At a second instance in time, just before light-emitting diode 210 is turned on, track-and-hold circuit 260 is switched to a "hold-mode". In other words, the last input level is hold and the last sample "tracked" in track mode is output. The loop within photoplethysmography sensor apparatus 200 then subtracts the current ambient level during a subsequent time period.

During said subsequent time period, light-emitting diode 210 is turned on. The stored ambient level is thus subtracted from the combined current $I_L+I_A$. Consequently, only the PPG signal (i.e., $I_L$), but not the current from the interfering ambient light (i.e., $I_A$), is amplified by a second amplifying unit 240, which may be, e.g., a TIA. The resulting output PPG signal from transimpedance amplifier 240 may preferably be stored in an optional sample-and-hold circuit. Alternatively and/or additionally, the resulting output PPG signal from transimpedance amplifier 240 may be converted directly by analog-to-digital converter 280.

At a fourth instance in time, light-emitting diode 210 is switched off again. The resulting setting may then be considered as the starting point for further ambient light suppression iteration by switching track-and-hold circuit 260 in the "track-mode" again and then proceeding as noted herein above. It is noted that ambient light correcting feedback loop 201 is preferably always closed, because of the tracking part of track-and-hold circuit 260. Consequently, that part of the signal is always insignificantly small within the loop. Namely, since PPG signals are small (especially in reflective mode PPG sensors), ambient light levels can be relatively high. If ambient part $I_A$ of the current was not continuously subtracted, transimpedance amplifier 240 would have to settle to large ambient light steps during each correction cycle. In the present configuration, this is not the case. The present embodiment thereby allows for relaxing the dynamic requirements on photoplethysmography sensor apparatus 200.

Figure 3:
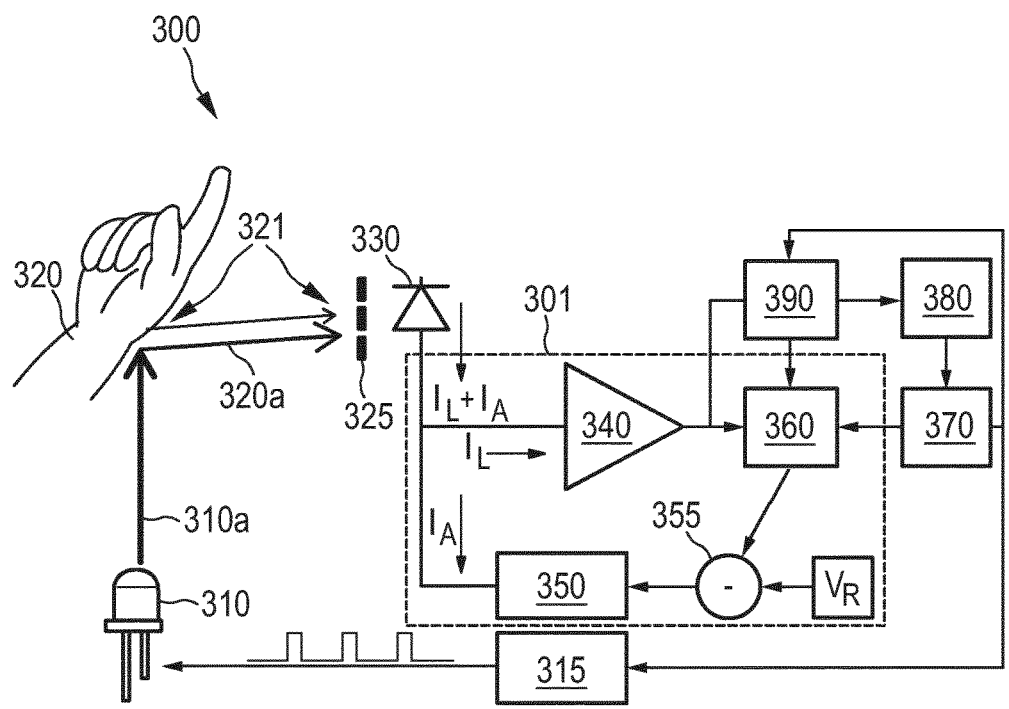
FIG. 3 shows schematically and exemplarily another embodiment of a photoplethysmography sensor apparatus.

FIG. 3 shows schematically and exemplarily another embodiment of a photoplethysmography sensor apparatus 300. Elements 3xx shown in FIG. 3 correspond to like-numbered elements 2xx in FIG. 2. In the embodiment shown in FIG. 3, a synchronous detector 390 is placed before analog-to-digital converter 380, to allow rejection or suppression of further interference (such as, e.g., from 1/f noise (i.e., noise where the power spectral density (energy or power per Hz) is inversely proportional to the frequency f of the noise signal) of transimpedance amplifier 340, and external interferences not synchronous with LED light 310a). External interferences not synchronous with LED light 310a may include, e.g., external electromagnetic current such as, e.g., 50/60 Hz power line interference picked up elsewhere in the circuit (i.e. not part of the photocurrent). These interferences may hence be rejected by synchronous detector 390. Synchronous detector 390 preferably comprises a synchronous rectifier followed by a low pass filter. The synchronous rectifier preferably multiplies the signal with +1 or −1. Rectification is preferably synchronous with the control of LED 310, the control being effected by means of LED driver 315.

In a further preferred embodiment, the synchronous detector 390 may be implemented as a digital lock-in amplifier in the microcontroller.

Figure 4:
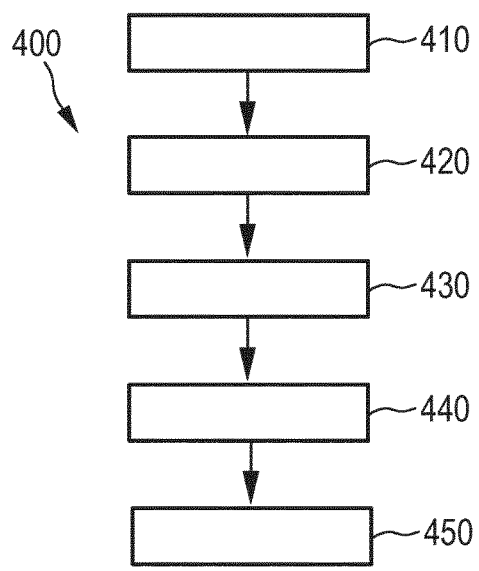
FIG. 4 shows schematically and exemplarily an embodiment of a photoplethysmography sensor method.

FIG. 4 shows schematically and exemplarily an embodiment of a photoplethysmography sensor method 400.

In step 410, a first light signal 210a, 310a is generated by a light source unit.

In step 420, a second light signal 220a, 320a is observed by a photodetector unit, wherein said second light signal 220a, 320a is indicative of an absorption of said first light signal 210a, 310a in a target 220, 320.

In step 430, a photodetector output signal is received by an ambient light compensating feedback loop (201, 301) comprising a track-and-hold unit (260, 360) and an amplifying unit (250, 350) in response to observing said second light signal 220a, 320a.

In step 440, an output signal of the track-and-hold unit 260, 360 is compared to a reference signal $V_R$, wherein said output signal of said track-and-hold unit 260, 360 is based on said photodetector output signal.

In step 450, a compensation current is provided by the amplifying unit (250, 350) to the track-and-hold unit (260, 360) based on said comparison.

The invention can be used in photoplethysmographic sensors, and in particular as a small and efficient photoplethysmographic front end. The invention can also be used in other pulse oximetry sensors, such as, e.g., $SpO_2$ sensors.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

The determinations and/or the control of the photoplethysmography sensor apparatus in accordance with the above described photoplethysmography sensor method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A photoplethysmography sensor apparatus comprising:
   a light source unit configured to generate a first light signal;
   a photodetector unit configured to observe a second light signal, where said second light signal is indicative of an absorption of said first light signal in a target, wherein said photodetector unit is further configured to output a photodetector output signal in response to observing said second light signal; and
   an ambient light compensating feedback loop comprising a track-and-hold unit configured to receive said photodetector output signal;
   wherein said photoplethysmography sensor apparatus is configured to compare an output signal of said track-and-hold unit to a reference signal ($V_R$), and wherein said ambient light compensating feedback loop comprises a first amplifying unit configured to provide a compensation current based on said comparison to the track-and-hold unit.

2. The photoplethysmography sensor apparatus of claim 1, further comprising a second amplifying unite for amplifying a sum of the compensation current and the photodetector output signal and for delivering an amplified signal to an input of the track-and-hold unit.

3. The photoplethysmography sensor apparatus of claim 2, wherein said second amplifying unit comprises a transimpedance amplifier.

4. The photoplethysmography sensor apparatus of claim 1, wherein said first amplifying unit comprises a trans-conductance amplifier, wherein said trans-conductance amplifier comprises a resistor and/or a voltage controlled current source.

5. The photoplethysmography sensor apparatus of claim 1, wherein said photoplethysmography sensor apparatus comprises an analog-to-digital converter configured to receive an output signal from said second amplifying unit.

6. The photoplethysmography sensor apparatus of claim 1, wherein said photoplethysmography sensor apparatus further comprises a light source driver unit configured to control said light source unit.

7. The photoplethysmography sensor apparatus of claim 1, wherein said photoplethysmography sensor apparatus further comprises a synchronous detector.

8. The photoplethysmography sensor apparatus of claim 7, wherein said photoplethysmography sensor apparatus further comprises a light source driver unit configured to control said light source unit and wherein said synchronous detector is configured to operate synchronously with said light source driver unit.

9. The photoplethysmography sensor apparatus of claim 7, wherein said photoplethysmography sensor apparatus comprises an analog-to-digital converter configured to receive the output signal from said synchronous detector.

10. The photoplethysmography sensor apparatus of claim 7, wherein said synchronous detector comprises a synchronous rectifier followed by a low pass filter.

11. The photoplethysmography sensor apparatus of claim 10, wherein said synchronous rectifier multiplies the signal with +1 or −1.

12. The photoplethysmography sensor apparatus of claim 1, wherein said photoplethysmography sensor apparatus further comprises a microcontroller configured to adjust said reference signal ($V_R$).

13. A photoplethysmography sensor method comprising the steps of:
- generating a first light signal by a light source unit;
- observing a second light signal by a photodetector unit, wherein said second light signal is indicative of an absorption of said first light signal in a target;
- receiving, in response to observing said second light signal, a photodetector output signal by an ambient light compensating feedback loop comprising a track-and-hold unit and an amplifying unit;
- comparing an output signal of the track-and-hold unit to a reference signal ($V_R$), wherein said output signal of said track-and-hold unit is based on said photodetector output signal; and
- providing a compensation current by the amplifying unit to the track-and-hold unit based on said comparison.

14. A photoplethysmography sensor computer program product comprising a computer readable memory storing computer program code means for causing a photoplethysmography sensor apparatus to carry out the following steps, when the program is run on a computer controlling the photoplethysmography sensor apparatus:
- generate a first light signal by a light source unit;
- observe a second light signal by a photodetector unit, wherein said second light signal is indicative of an absorption of said first light signal in a target;
- receive, in response to observing said second light signal, a photodetector output signal by an ambient light compensating feedback loop comprising a track-and-hold unit and an amplifying unit;
- compare an output signal of the track-and-hold unit to a reference signal ($V_R$), wherein said output signal of said track-and-hold unit is based on said photodetector output signal; and
- provide a compensation current by the amplifying unit to the track-and-hold unit based on said comparison.

* * * * *